(12) United States Patent
Bendix et al.

(10) Patent No.: US 12,427,264 B2
(45) Date of Patent: Sep. 30, 2025

(54) DRUG DELIVERY DEVICE WITH PLUNGER ROD HAVING NONUNIFORM STOPPER INTERFACE

(71) Applicant: Novo Nordisk A/S, Bagsvaerd (DK)

(72) Inventors: Klaus Bendix, Smoerum (DK); Daniel Patrick Godskesen True, Hellerup (DK); Dan Noertoft Soerensen, Alleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 946 days.

(21) Appl. No.: 17/619,898

(22) PCT Filed: Jun. 26, 2020

(86) PCT No.: PCT/EP2020/068013
§ 371 (c)(1),
(2) Date: Dec. 16, 2021

(87) PCT Pub. No.: WO2020/260576
PCT Pub. Date: Dec. 30, 2020

(65) Prior Publication Data
US 2022/0305211 A1    Sep. 29, 2022

(30) Foreign Application Priority Data

Jun. 28, 2019 (EP) .................... 19183155

(51) Int. Cl.
*A61M 5/315* (2006.01)
*A61M 5/20* (2006.01)
*A61M 5/32* (2006.01)

(52) U.S. Cl.
CPC ...... *A61M 5/31596* (2013.01); *A61M 5/2033* (2013.01); *A61M 5/31515* (2013.01);
(Continued)

(58) Field of Classification Search
CPC ............ A61M 5/31596; A61M 5/2033; A61M 5/31515; A61M 5/3202; A61M 2005/202;
(Continued)

(56) References Cited

U.S. PATENT DOCUMENTS

| 4,394,863 A | 7/1983 | Bartner |
| 9,220,844 B2 | 12/2015 | Heinz |

(Continued)

FOREIGN PATENT DOCUMENTS

| JP | 2000237312 A | * | 9/2000 | .......... A61M 5/1409 |
| JP | 2018501852 A | | 1/2018 | |

(Continued)

*Primary Examiner* — James D Ponton
(74) *Attorney, Agent, or Firm* — Wesley Nicolas

(57) ABSTRACT

The present invention provides a drug delivery device (1) comprising: a drug reservoir (20) comprising a reservoir body (21) extending along a reference axis and an elastomeric stopper (30) arranged in the reservoir body (21), the elastomeric stopper (30) comprising a stopper body (31) extending between a front stopper end (32) and a rear stopper end (34) and having a plurality of axially spaced apart circumferential ribs (33) for sealing interaction with an interior wall (22) of the reservoir body (21), and a plunger rod structure (10) for displacing the elastomeric stopper (30) relative to the interior wall (22), the plunger rod structure (10) extending along the reference axis and comprising a distal end face (12, 14) adapted to interface with the rear stopper end (34). The distal end face (12, 14) comprises a first force transferring portion (14) and a second force transferring portion (12), the first force transferring portion (14) axially leading the second force transferring portion (12) and being adapted to interact with a peripheral portion of the rear stopper end (34).

18 Claims, 2 Drawing Sheets

(52) U.S. Cl.
CPC ..... *A61M 5/3202* (2013.01); *A61M 2005/202* (2013.01); *A61M 2005/31598* (2013.01)

(58) Field of Classification Search
CPC ......... A61M 2005/31598; A61M 2005/31521; A61M 5/31513; A61M 5/31; A61M 5/3213

See application file for complete search history.

(56) References Cited

U.S. PATENT DOCUMENTS

| | | |
|---|---|---|
| 9,592,346 B2 | 3/2017 | Quinn et al. |
| 10,765,811 B2 | 9/2020 | Vedrine et al. |
| 10,786,628 B2 | 9/2020 | Jacobsen |
| 2015/0198248 A1* | 7/2015 | Kiilerich ................. A61M 5/24 92/172 |
| 2016/0151586 A1* | 6/2016 | Kemp ................. A61M 5/2033 604/198 |
| 2018/0049948 A1* | 2/2018 | Egeland ................ A61M 5/315 |
| 2018/0243508 A1 | 8/2018 | Berg et al. |

FOREIGN PATENT DOCUMENTS

| | | |
|---|---|---|
| JP | 2018509260 A | 4/2018 |
| WO | 9530444 A1 | 11/1995 |
| WO | 0062839 A2 | 10/2000 |
| WO | 2010/139793 A1 | 12/2010 |
| WO | 2017157396 A1 | 9/2017 |
| WO | 2018206494 A1 | 11/2018 |

\* cited by examiner

DRUG DELIVERY DEVICE WITH PLUNGER ROD HAVING NONUNIFORM STOPPER INTERFACE

CROSS-REFERENCE TO RELATED APPLICATIONS

This application is a 35 U.S.C. § 371 National Stage application of International Application PCT/EP2020/068013 (published as WO 2020/260576), filed Jun. 26, 2020, which claims priority to European Patent Application 19183155.1, filed Jun. 28, 2019; the contents of which are incorporated herein by reference.

FIELD OF THE INVENTION

The present invention relates to medical devices and more particularly to drug delivery devices with reservoirs having a volume which can be reduced by displacement of a piston or stopper.

BACKGROUND OF THE INVENTION

Within some medical treatment areas, a combination therapy involving co-administration of at least two drugs is advantageous because of synergistic or additive effects. For example, within diabetes care, in the management of type 2 diabetes mellitus, concomitant use of certain insulin and glp-1 products has been shown to reduce $HbA_{1c}$ levels in subjects, thereby improving glycaemic control.

Many drugs must be administered parenterally to be effective in the body and some of these, e.g. insulin and glp-1, may require one or more doses to be delivered subcutaneously on a daily basis. Subcutaneous drug delivery is often associated with discomfort as many people dislike the thought of having an injection needle inserted through the skin. An undisclosed number of people even suffer from needle-phobia, and these people have a particularly strong desire to escape multiple daily injection therapy.

One attractive scenario, therefore, is to reduce the number of required skin penetrations by administering the drugs at the same time, or substantially the same time, through a single injection needle. In some cases, this is achievable by co-formulation of the active ingredients, where the co-formulated product is administered using a conventional injection device. In other cases, e.g. if the active ingredients are unsuitable for co-formulation, the individual substances are stored in separate chambers of a dual chamber, or multi-chamber, reservoir device from which they can be expressed, simultaneously or sequentially, through a single injection needle by use of dedicated expressing means.

U.S. Pat. No. 4,394,863 (Survival Technology, Inc.) discloses an example of a dual chamber reservoir device in the form of an automatic injector with a cartridge having a fixedly mounted hypodermic needle. In a pre-use state of the device the cartridge holds a forward liquid medicament in a front chamber and a rearward liquid medicament in a rear chamber. The two liquids are separated by an intermediate piston, and the rear chamber is sealed proximally by a rearward piston. During use, in response to a release of a stressed spring, a plunger is urged forward, pushing the rearward piston and pressurising the rearward liquid medicament which transmits the movement of the rearward piston to the intermediate piston. Eventually, as the spring continues to provide a forward bias to the plunger, this leads to an expelling of the forward liquid medicament through the hypodermic needle, followed by an expelling of the rearward liquid medicament, via a distally arranged bypass section.

WO 2010/139793 (Novo Nordisk A/S) discloses an example of a dual chamber reservoir device in the form of a manually operated mixing device with a piston coupling arrangement allowing for an aspiration procedure to ensure proper insertion of an associated IV infusion needle. In a pre-use state of the device a dry drug, or a liquid, is held in a front chamber, and a liquid is held in a rear chamber. The two substances are separated by a front piston, and the rear chamber is sealed proximally by a rear piston through which a piston rod extends. During use the piston rod is manually advanced, slaving the rear piston and pressurising the rear chamber liquid which transmits the movement of the rear piston to the front piston. As the user continues to press the piston rod forward the front piston enters a bypass section and becomes immobilised because the pressure now forces the rear chamber liquid into the bypass, past the front piston and into the front chamber. In the front chamber the two substances mix as the rear chamber collapses. When the rear piston eventually reaches the front piston and the substances are thoroughly mixed the user can expel the mixed substance by continued advancement of the piston rod.

A common drawback of such devices is the fact that during storage, over time, the piston material tends to adhere to the reservoir material, which means that a significant static friction must be overcome in order to initiate a drug mixing and/or expelling. Due to the incompressibility of the liquid in the rear chamber the two pistons will move in unison until the front piston reaches the bypass section. Resultantly, the force required to overcome this static friction is actually the sum of the forces required to break loose the individual pistons.

In case of a manually driven piston rod the sudden shift from static to kinetic friction as the pistons break loose is likely to cause a jerking forward motion of the pistons as the user tries to compensate for the sudden acceleration by significantly decreasing the force input. Apart from being an unpleasant user experience it may in fact lead to an overly fast transfer of the rear chamber liquid to the front chamber. If the front chamber carries a dry powder to be reconstituted the transfer process may even lead to undesired foaming.

In connection with spring driven injection devices like the automatic injector of U.S. Pat. No. 4,394,863 the spring needs to be relatively powerful to ensure availability of a sufficient break-loose force. A downside of this is that once the friction becomes kinetic the power available for the actual drug expelling is very high and may lead to an unpleasantly high speed of delivery. Adding to that, a powerful spring requires stronger interfacing injection device parts to avoid creep or breakage during a potential medium- or long-term storage period in pre-loaded state, increasing both the cost and the weight of the injection device.

The described adherence of the piston material to the reservoir material may in fact be a challenge for single chamber reservoirs as well, even though only one piston needs to be mobilised and the required break loose force is relatively smaller. Hence, the problems related to overcoming the static friction and controlling the speed of delivery are also pertinent to such devices as e.g. conventional syringes and automatic injection pens employing conventional drug cartridges.

SUMMARY OF THE INVENTION

It is an object of the invention to eliminate or reduce at least one drawback of the prior art, or to provide a useful alternative to prior art solutions.

In particular, it is an object of the invention to provide a drug delivery device having means for reducing the force required to set one or more pistons, or stoppers, in motion.

It is a further object of the invention to provide a drug delivery device having means for enabling a more uniform piston displacement force throughout a drug administration procedure.

In the disclosure of the present invention, aspects and embodiments will be described which will address one or more of the above objects and/or which will address objects apparent from the following text.

In one aspect the invention provides a drug delivery device according to claim 1.

Hence, a drug delivery device is provided comprising a drug reservoir comprising a reservoir body extending along a reference axis and an elastomeric stopper arranged in the reservoir body. The elastomeric stopper comprises a stopper body which extends between a front stopper end and a rear stopper end and has a plurality of axially spaced apart circumferential ribs for sealing interaction with an interior wall of the reservoir body, e.g. as specified in ISO 11040-5 (2012): Prefilled syringes—part 5: Plunger stoppers for injectables. The drug delivery device further comprises a plunger rod structure for displacing the elastomeric stopper relative to the interior wall. The plunger rod structure comprises a distal end face adapted to interface with the rear stopper end. The distal end face comprises a first force transferring portion and a second force transferring portion. The first force transferring portion is positioned distally of the second force transferring portion and is adapted to interact with a peripheral portion of the rear stopper end. In the present context "a peripheral portion" of a structure having a given extent in a transversal direction from a central axis is a portion of that structure which is positioned more than half of the given extent away from the central axis along that transversal direction.

The first force transferring portion thus leads the second force transferring portion when the plunger rod structure moves distally along the reference axis to displace the elastomeric stopper. This results in a nonuniform pressure being exerted onto the rear stopper end, where initially a non-zero pressure is exerted onto the peripheral portion and zero pressure is exerted onto the remaining portion of the rear stopper end. The pressure on the peripheral portion causes a local breaking loose of rear stopper material from the interior wall such that when the second force transferring portion reaches the rear stopper end the bulk stopper displacement is achieved more easily because some of the stickiness has already been overcome. As a consequence of the sequential detachment of the circumferential ribs from the reservoir body the maximum force needed to activate the elastomeric stopper is reduced and the overall force profile for a complete drug expelling action with the drug delivery device is more homogenous.

The distal end face may be designed in various ways to obtain the desired effect, but, generally, the effect correlates with the position and the configuration of the first force transferring portion. For example, if the rear stopper end is circular with a centre the first force transferring portion may be arranged to abut an area of the rear stopper end positioned a radial distance from the centre which exceeds half, or two thirds, of the radius of the circle which the rear stopper end spans. The closer the area of contact between the first force transferring portion and the rear stopper end is to the interior wall of the reservoir body the greater the effect of the pressure provided by the first force transferring portion vis-à-vis the aspired reduction of the break loose force.

Likewise, for example, the peripheral portion may be less than semi-circular in size to maximise the local pressure effect.

In exemplary embodiments of the invention the first force transferring portion has a radial extent in the range of [1 mm; 2 mm]. In certain of these embodiments the first force transferring portion has a radial extent of 2 mm, or approximately 2 mm.

The first force transferring portion and the second force transferring portion may have an accumulated surface area which substantially equals a total surface area of the rear stopper end. Thereby, the elastomeric stopper will be supported during displacement over the entire, or substantially entire, rear stopper end.

The second force transferring portion may be orthogonal to the reference axis, and the first force transferring portion may form part of a stud member which protrudes distally from the second force transferring portion. The surface of the plunger rod structure interacting with the majority of the rear stopper end thus conforms thereto, ensuring that the elastomeric stopper does not tilt during bulk advancement in the drug reservoir.

The stud may be adapted to abut the rear stopper end at an interface between one of the plurality of axially spaced apart circumferential ribs and the interior wall, maximising the effect of the initial pressure provided by the first force transferring portion.

In exemplary embodiments of the invention the stud has an axial dimension in the range of [1 mm; 2 mm].

The distal end face may alternatively exhibit a wave-like profile having a crest at a peripheral portion of the distal end face. The crest then constitutes the first force transferring portion and axially leads the remainder of the distal end face which constitutes the second force transferring portion.

The distal end face may alternatively exhibit a parabolic profile, in which case the first force transferring portion is adapted to exert a pressure onto diametrically opposite peripheral portions of the rear stopper end to thereby initially cause a local breaking loose of stopper material from the interior wall of the reservoir body at two different locations.

In exemplary embodiments of the invention the drug delivery device further comprises a housing, and the plunger rod structure comprises a hollow interior adapted to accommodate a compression spring element releasable to displace the plunger rod structure distally relative to the housing.

The drug reservoir may further comprise a second elastomeric stopper arranged distally of the elastomeric stopper, and a bypass section for allowing fluid flow past the second elastomeric stopper during displacement of the elastomeric stopper relative to the interior wall. In that case the drug reservoir is of the above described dual chamber type which normally exhibits relatively large break-loose forces as a consequence of the fact that the two elastomeric stoppers must be mobilised simultaneously. With a plunger rod structure of the herein defined type the maximum input force to execute a drug expelling action can be reduced significantly.

In another aspect the invention provides a plunger rod structure for displacing an elastomeric stopper of the type comprising a stopper body extending axially between a front stopper end and a rear stopper end and having a plurality of axially spaced apart circumferential sealing ribs along a wall of a drug reservoir, the plunger rod structure comprising a distal end face adapted to interface with the rear stopper end, wherein the distal end face comprises a first force transferring portion and a second force transferring portion, the first force transferring portion axially leading the second force transferring portion at a periphery of the distal end face.

Such a plunger rod structure will engage, and apply an axial force to, a peripheral portion of the rear stopper end before interacting with a remaining portion of the rear stopper end, thereby providing a sequential detachment of the sealing ribs from the wall of the drug reservoir and resultantly requiring a lower axial input force to set the elastomeric stopper in motion. The plunger rod structure may specifically be configured as described above.

It is noted that an elastomeric stopper as described in relation to the present invention may be made entirely or partially of an elastomeric material, the outer surface interfacing with the reservoir, however, naturally being elastomeric to obtain the desired sealing effect.

For the avoidance of any doubt, in the present context the term "drug" designates a medium which is used in the treatment, prevention or diagnosis of a condition, i.e. including a medium having a therapeutic or metabolic effect in the body. Further, the terms "distal" and "proximal" denote positions at, or directions along, a drug delivery device, a drug reservoir, or a needle unit, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When/If relative expressions, such as "upper" and "lower", "left" and "right", "horizontal" and "vertical", "clockwise" and "counter-clockwise", etc., are used in the following, these refer to the appended figures and not necessarily to an actual situation of use. The shown figures are schematic representations for which reason the configuration of the different structures as well as their relative dimensions are intended to serve illustrative purposes only.

Figure 1:
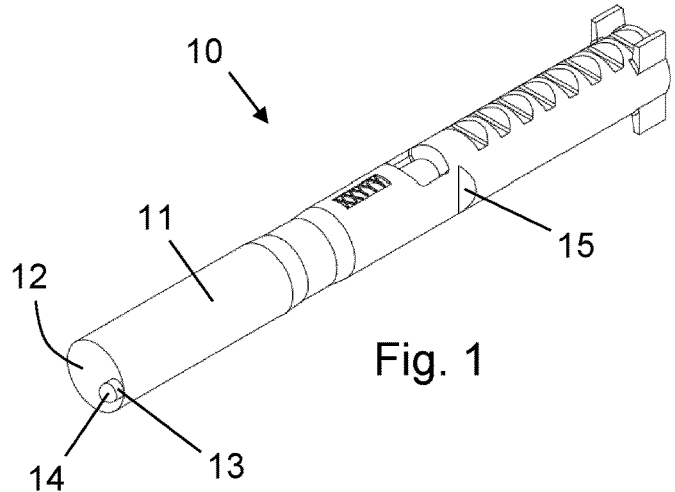
FIG. 1 is a perspective view of a plunger rod structure according to an exemplary embodiment of the invention.

FIG. 1 is a perspective view of a plunger rod 10 for use in a drug delivery device according to an embodiment of the invention. The plunger rod 10 comprises a hollow elongated shaft 11 which extends along a longitudinal axis. At its front end the plunger rod 10 is provided with an abutment surface 12 adapted to abut a stopper in a drug reservoir during a drug administration action, as explained in more detail below. A peripheral stud 13 protrudes distally from the abutment surface 12 and has a leading end 14 for preparing stopper movement, as also explained below. The plunger rod 10 is further provided with a pair of diametrically opposite notches 15.

Figure 2:
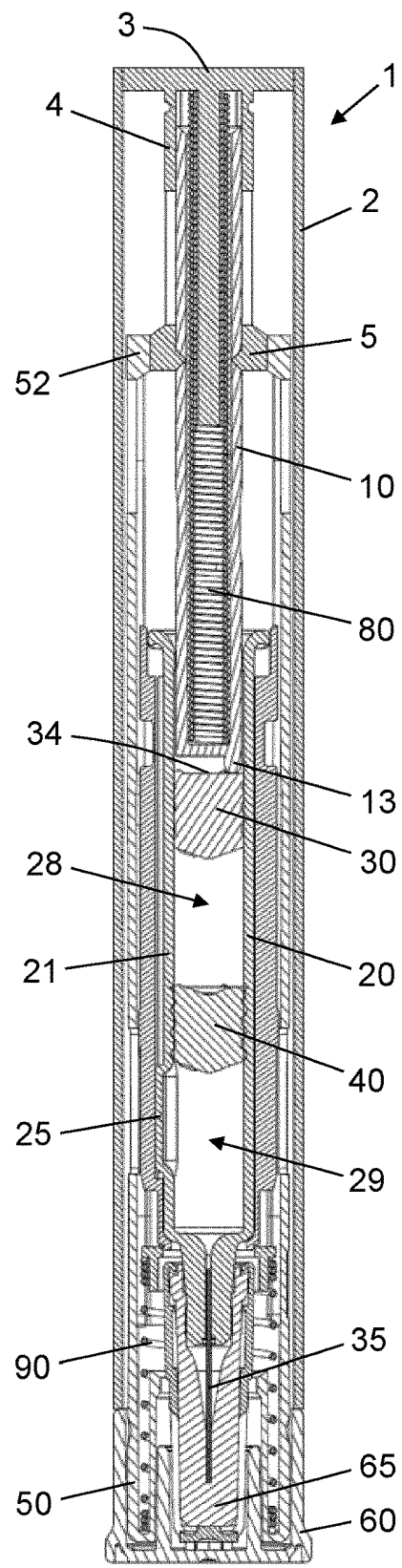
FIG. 2 is a longitudinal section view of a drug delivery device according to an exemplary embodiment of the invention, including the plunger rod structure of FIG. 1.

FIG. 2 is a longitudinal section view of an injection device 1 according to an exemplary embodiment of the invention employing the plunger rod 10. The injection device 1 comprises a housing 2 which accommodates a syringe 20 having a barrel 21 extending along a general axis coinciding with the longitudinal axis of the plunger rod 10. The barrel 21 is generally circular cylindrical but has a distal evagination forming a bypass channel 25 as well as a narrowed distal end portion holding an injection needle 35. A front stopper 40 is arranged proximally of the bypass channel 25, providing a proximal seal for a front chamber 29 holding a first liquid substance, and a rear stopper 30 is arranged proximally of, and axially spaced apart from, the front stopper 40, thereby providing a proximal seal for a rear chamber 28 holding a second liquid substance.

In the shown pre-use state of the injection device 1 the leading end 14 of the stud 13 abuts a proximal end 34 of the rear stopper 30, but the abutment surface 12 is spaced apart from the rear stopper 30. A pre-strained drive spring 80 is arranged in the hollow of the plunger rod 10, proximally abutting an interior face of an end wall 3 of the housing 2. A pair of radially pliable arms 4 extend distally from the end wall 3, and the plunger rod 10 is held in position by a claw 5 on each arm 4 wedging into one of the notches 15, each claw 5 being restrained radially by a retaining edge 52 of a needle shield 50 extending axially between the syringe 20 and the housing 2.

The needle shield 50 is biased distally by a shield spring 90 and is axially displaceable along the syringe 20 against this bias to expose the injection needle 35. The final product offered by the manufacturer includes a needle cap 60 attached to the housing 2 for covering the needle shield 50, and the needle cap 60 carries an inner cover 65 for dedicated protection of the injection needle 35.

To perform a drug administration the user simply removes the needle cap 60, places the needle shield 50 against a skin surface and presses the housing 2 towards the skin, thereby compressing the shield spring 90 and displacing the needle shield 50 to allow the injection needle 35 to enter the desired injection site.

As the needle shield 50 is thus displaced the retaining edge 52 slides past the claws 5, allowing the arms 4 to deflect radially. Consequently, the force from the pre-strained drive spring 80 immediately urges the claws 5 radially out of the notches 15, whereby the plunger rod 10 is unlatched and the drive spring 80 is released.

Figure 3:
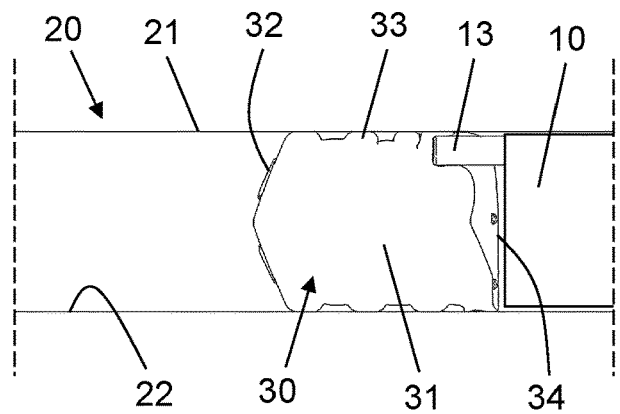
FIG. 3 is a side view of a distal portion of the plunger rod structure interacting with an elastomeric stopper in the drug delivery device.

FIG. 3 illustrates the initial interaction between the plunger rod 10 and the rear stopper 30 at the release of the drive spring 80. The rear stopper 30 comprises an elastomeric stopper body 31, which extends between a distal end 32 and the proximal end 34 and has four axially spaced apart circumferential ribs 33 providing a fluid tight sealing interface to an inner wall 22 of the barrel 21.

In order to set the rear stopper 30 in motion the static friction between the circumferential ribs 33 and the inner wall 22 must be overcome. Once the static friction is overcome and the rear stopper 30 begins to move the interface between the stopper body 31 and the barrel 21 exhibits a dynamic friction which is smaller then the static friction. Hence, the effort required to carry out a drug administration action depends to a large extent on the size of the so-called break-loose force.

Compared to a corresponding single chamber injection device the break-loose force for the injection device 1 is twice as large because the rear stopper 30 and the front stopper 40 are set in motion simultaneously due to the second liquid substance in the rear chamber 28 being incompressible. Hence, a solution that could reduce the break-loose force would allow the manufacturer of the injection device 1 to incorporate a less powerful drive spring and thereby reduce the risk of interfacing components deforming under the load from the pre-strained spring during shelving.

The solution provided by the present embodiment of the invention is the addition of the stud 13 on the peripheral portion of the abutment surface 12, which provides a leading interface that interacts with a peripheral portion of the proximal end 34 of the rear stopper 30 before the abutment surface 12 interacts with the remaining portion of the proximal end 34. In FIG. 3 the relative dimension of the stud 13 is exaggerated to more clearly illustrate its effect. When the plunger rod 10 advances towards the distal end of the syringe 20 the leading end 14 initially exerts a pressure onto a peripheral portion of the proximal end 34 while the abutment surface 12 approaches the rear stopper 30. This will deform the peripheral portion of the proximal end 34 and eventually result in a local breaking loose of rear stopper 30 material from the barrel 21 in the interface between the proximal most of the circumferential ribs 33 and the inner wall 22.

Figure 4:
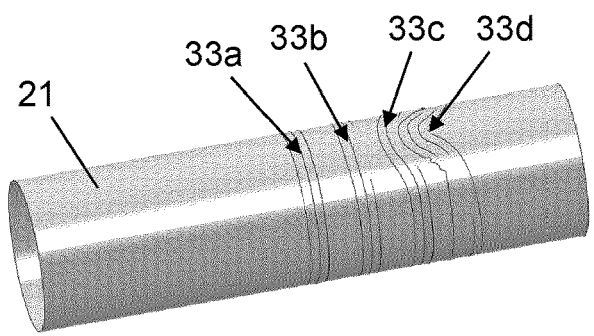
FIG. 4 is a diagrammatic illustration of an initial deformation of the elastomeric stopper resulting from the interaction with the plunger rod structure.

So, when the abutment surface 12 moments later makes contact with the proximal end 34 the intrusion of the stud 13 into the elastomeric stopper body 31 will already have displaced some of the rear stopper 30 periphery relative to the inner wall 22. This is illustrated in FIG. 4, where the solid line clusters on the exterior of the barrel 21 represent the position of the respective circumferential ribs 33 along the inner wall 22. It is seen that the proximal most circumferential rib, sketched by contact lines 33*d*, is locally deflected in the distal direction, the circumferential rib adjacent to the proximal most circumferential rib, sketched by contact lines 33*c*, is deflected a little less, the one adjacent to that, sketched by contact lines 33*b*, only slightly, and the distal most circumferential rib, sketched by contact lines 33*a*, is yet unaffected.

The local initial deflection of the circumferential ribs 33, prompted by the local, relatively high, pressure provided by the leading end 14, positively contributes to a reduction of the break-loose force needed to mobilise the rear stopper 30 and the front stopper 40 in the barrel 21. The sequential detachment of the circumferential ribs 33 from the inner wall 22 increases the effect of the drive spring 80 because not all contact points between the two stoppers and the inner wall 22 then need to be broken at the same time.

To ensure that the rear stopper 30 does not tilt in the barrel 21, which might result in leakage, the axial dimension of the stud 13 should be limited relative to the axial dimension of the rear stopper 30. In the present case the axial dimension of the stud 13 is 2 mm. Thereby, following the initial activation by the leading end 14 the abutment surface 12 takes over and provides a stable and even support for the advancement of the rear stopper 30 as the drive spring 80 continues to release energy.

The level of reduction of the break-loose force is dependent on the friction in the barrel/stopper interface. Unsurprisingly, the effect of the stud 13 is higher in high friction systems. For example, in simulations using a coefficient of friction of approximately 0.3 the break-loose force is reduced to about ⅓ of the break-loose force for a conventional plunger rod design.

Similar to the conventional mode of operation of a dual chamber injection device once the bulk of the rear stopper 30 is set in motion and advances through the barrel 21 the second liquid substance pushes the front stopper 40 towards, and eventually into, the bypass channel 25, while causing a volume of the first liquid substance to pass through the injection needle 35. When the front stopper 40 reaches the bypass channel 25 the continued advancement of the rear stopper 30 causes the second liquid substance to pass the front stopper 40 and enter the front chamber 29 where it mixes with the remaining volume of the first liquid substance and is flushed through the injection needle 35 therewith.

Figure 5:
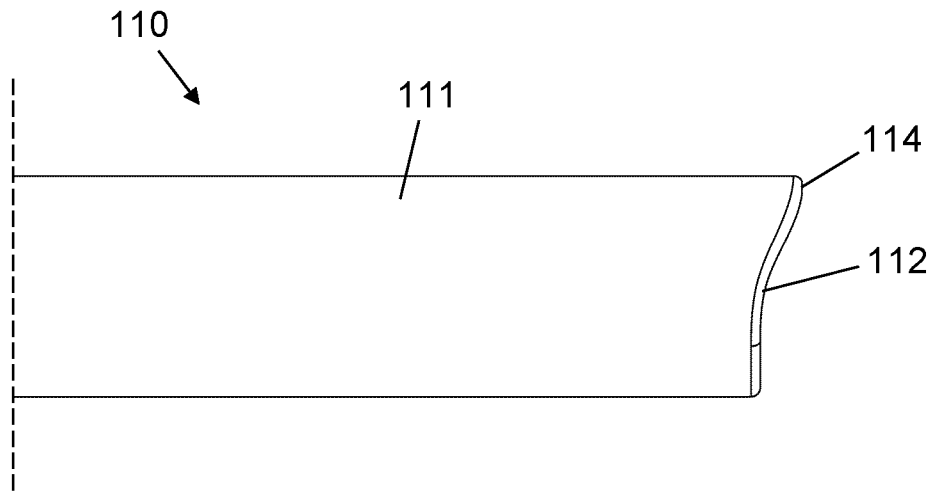
FIG. 5 is a side view of a distal portion of a plunger rod structure according to another exemplary embodiment of the invention.

FIG. 5 is a side view of a distal portion of a plunger rod 110 according to another embodiment of the invention. The plunger rod 110 comprises an elongated shaft 111 which extends along a longitudinal axis and which at its front end is provided with a wave-shaped abutment surface 112 for interaction with a stopper in a drug reservoir. The abutment surface 112 is formed to provide a crest 114 at a peripheral portion of the shaft 111. The crest 114 axially leads the remaining portions of the abutment surface 112 and thus has a similar effect as the leading end 14 of the stud 13 on the plunger rod 10 described above. The shaft 111 could either be hollow, in which case the plunger rod 110 could be employed in the injection device 1 as an alternative to the plunger rod 10, or solid.

Figure 6:
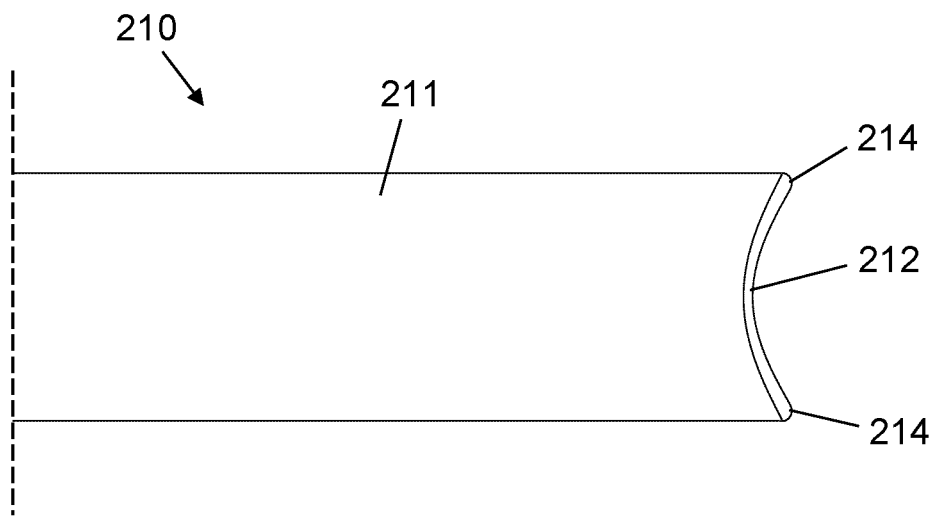
FIG. 6 is a side view of a distal portion of a plunger rod structure according to a further exemplary embodiment of the invention.

FIG. 6 is a side view of a distal portion of a plunger rod 210 according to a further embodiment of the invention. The plunger rod 210 comprises an elongated shaft 211 which extends along a longitudinal axis and has an abutment surface 212 at its front end for interaction with a stopper in a drug reservoir. The abutment surface 212 has a parabolic profile, providing two protruding portions 214 at diametrically opposite peripheral portions of the shaft 211. Each of the protruding portions 214 has a similar effect as the leading end 14 of the stud 13 on the plunger rod 10 described above, whereby, initially, a local disengagement of stopper material from two circumferentially spaced apart interior portions of the drug reservoir is obtained. The shaft 211 could either be hollow, in which case the plunger rod 210 could be employed in the injection device 1 as an alternative to the plunger rod 10, or solid.

The invention claimed is:

1. A drug delivery device comprising:
a drug reservoir comprising a reservoir body extending along a reference axis and a first elastomeric stopper arranged in the reservoir body, the first elastomeric stopper comprising a stopper body extending between a front stopper end and a rear stopper end and having a plurality of axially spaced apart circumferential ribs for sealing interaction with an interior wall of the reservoir body, and
a plunger rod structure for displacing the first elastomeric stopper relative to the interior wall, the plunger rod structure extending along the reference axis and comprising a distal end face adapted to interface with the rear stopper end,
wherein the distal end face comprises a first force transferring portion and a second force transferring portion, the first force transferring portion axially leading the second force transferring portion and being adapted to interact with a peripheral portion of the rear stopper end$_2$
wherein the second force transferringportion is orthogonal to the reference axis, and wherein the first force transferring portion forms part of a stud which protrudes distally from the second force transferring portion, and
wherein the stud has an axial dimension of 1 mm to 2 mm.

2. A drug delivery device according to claim 1, wherein the peripheral portion of the rear stopper end is less than semi-circular.

3. A drug delivery device according to claim 1, wherein the stud has a maximum radial dimension of 2 mm.

4. A drug delivery device according to claim 1, wherein the stud is adapted to abut the rear stopper end at an interface between one of the plurality of axially spaced apart circumferential ribs and the interior wall.

5. A drug delivery device according to claim 1, further comprising a housing, wherein the plunger rod structure comprises a hollow interior adapted to accommodate a compression spring element releasable to displace the plunger rod structure distally relative to the housing.

6. A drug delivery device according to claim 1, wherein the drug reservoir further comprises a second elastomeric stopper arranged distally of the first elastomeric stopper, and a bypass section for allowing fluid flow past the second elastomeric stopper during displacement of the first elastomeric stopper relative to the interior wall.

7. A drug delivery device comprising:
a drug reservoir comprising a reservoir body extending along a reference axis and a first elastomeric stopper arranged in the reservoir body, the first elastomeric stopper comprising a stopper body extending between a front stopper end and a rear stopper end and having a plurality of axially spaced apart circumferential ribs for sealing interaction with an interior wall of the reservoir body, and
a plunger rod structure for displacing the first elastomeric stopper relative to the interior wall, the plunger rod structure extending along the reference axis and comprising a distal end face adapted to interface with the rear stopper end,
wherein the distal end face comprises a first force transferring portion and a second force transferring portion, the first force transferring portion axially leading the second force transferring portion and being adapted to interact with a peripheral portion of the rear stopper end,
wherein the second force transferring portion is orthogonal to the reference axis, and wherein the first force transferring portion forms part of a stud which protrudes distally from the second force transferring portion, and
wherein the stud has a maximum radial dimension of 2 mm.

8. A drug delivery device according to claim 7, wherein the peripheral portion of the rear stopper end is less than semi-circular.

9. A drug delivery device according to claim 7, wherein the stud has an axial dimension of 1 mm to 2 mm.

10. A drug delivery device according to claim 7, wherein the stud is adapted to abut the rear stopper end at an interface between one of the plurality of axially spaced apart circumferential ribs and the interior wall.

11. A drug delivery device according to claim 7, further comprising a housing, wherein the plunger rod structure comprises a hollow interior adapted to accommodate a compression spring element releasable to displace the plunger rod structure distally relative to the housing.

12. A drug delivery device according to claim 7, wherein the drug reservoir further comprises a second elastomeric stopper arranged distally of the first elastomeric stopper, and a bypass section for allowing fluid flow past the second elastomeric stopper during displacement of the first elastomeric stopper relative to the interior wall.

13. A drug delivery device comprising:
a drug reservoir comprising a reservoir body extending along a reference axis and a first elastomeric stopper arranged in the reservoir body, the first elastomeric stopper comprising a stopper body extending between a front stopper end and a rear stopper end and having a plurality of axially spaced apart circumferential ribs for sealing interaction with an interior wall of the reservoir body, and
a plunger rod structure for displacing the first elastomeric stopper relative to the interior wall, the plunger rod structure extending along the reference axis and comprising a distal end face adapted to interface with the rear stopper end,
wherein the distal end face comprises a first force transferring portion and a second force transferring portion, the first force transferring portion axially leading the second force transferring portion and being adapted to interact with a peripheral portion of the rear stopper end,
wherein the second force transferringportion is orthogonal to the reference axis, and wherein the first force transferring portion forms part of a stud which protrudes distally from the second force transferring portion, and
wherein the stud is adapted to abut the rear stopper end at an interface between one of the plurality of axially spaced apart circumferential ribs and the interior wall.

14. A drug delivery device according to claim 13, wherein the peripheral portion of the rear stopper end is less than semi-circular.

15. A drug delivery device according to claim 13, wherein the stud has an axial dimension of 1 mm to 2 mm.

16. A drug delivery device according to claim 13, wherein the stud has a maximum radial dimension of 2 mm.

17. A drug delivery device according to claim 13, further comprising a housing, wherein the plunger rod structure comprises a hollow interior adapted to accommodate a compression spring element releasable to displace the plunger rod structure distally relative to the housing.

18. A drug delivery device according to claim 13, wherein the drug reservoir further comprises a second elastomeric stopper arranged distally of the first elastomeric stopper, and a bypass section for allowing fluid flow past the second elastomeric stopper during displacement of the first elastomeric stopper relative to the interior wall.

\* \* \* \* \*

UNITED STATES PATENT AND TRADEMARK OFFICE
CERTIFICATE OF CORRECTION

| | | |
|---|---|---|
| PATENT NO. | : 12,427,264 B2 | Page 1 of 1 |
| APPLICATION NO. | : 17/619898 | |
| DATED | : September 30, 2025 | |
| INVENTOR(S) | : Klaus Bendix et al. | |

It is certified that error appears in the above-identified patent and that said Letters Patent is hereby corrected as shown below:

In the Claims

At Column 9, Claim 1, Line 20, delete "end2" and insert -- end, --.

At Column 9, Claim 1, Line 21, delete "transferringportion" and insert -- transferring portion --.

At Column 10, Claim 13, Line 45, delete "transferringportion" and insert -- transferring portion --.

Signed and Sealed this
Third Day of February, 2026

John A. Squires
*Director of the United States Patent and Trademark Office*